(12) United States Patent
Elmaleh et al.

(10) Patent No.: US 6,187,286 B1
(45) Date of Patent: Feb. 13, 2001

(54) TUMOR IMAGING AGENTS, METHODS AND KITS

(75) Inventors: David R. Elmaleh, Boston; John W. Babich, Belmont, both of MA (US)

(73) Assignee: The General Hospital Corporation, Boston, MA (US)

( * ) Notice: Under 35 U.S.C. 154(b), the term of this patent shall be extended for 0 days.

(21) Appl. No.: 08/846,999

(22) Filed: May 1, 1997

Related U.S. Application Data

(63) Continuation-in-part of application No. PCT/US96/20675, filed on Dec. 27, 1996.
(51) Int. Cl.⁷ .......................... A61K 51/00; A61M 36/14
(52) U.S. Cl. ...................... 424/1.73; 424/1.11; 424/1.65; 536/27.6; 536/27.7
(58) Field of Search .............................. 424/9.1, 9.3, 9.4, 424/9.5, 9.6, 9.7, 1.11, 1.65, 1.73; 206/223, 569, 570; 536/27.6, 27.7, 26.26, 26.8, 26.72, 27.1, 26.1; 534/7, 10–16

(56) References Cited

U.S. PATENT DOCUMENTS

| 5,476,928 | * | 12/1995 | Ward et al. ............................ 536/24 |
| 5,556,982 | * | 9/1996 | Fritzberg et al. ................. 548/303.7 |
| 5,684,148 | * | 11/1997 | Caruthers et al. .................. 536/26.1 |

OTHER PUBLICATIONS

Elmaleh et al (1984), Proc. Natl. Acad. Sci., USA, vol. 81, pp. 918–921, Feb. 1984.*

* cited by examiner

*Primary Examiner*—Dameron Jones
(74) *Attorney, Agent, or Firm*—Foley, Hoag & Eliot LLP

(57) ABSTRACT

The invention provides tumor imaging agents comprising a radionuclide in association with a nucleotide polyphosphate targeting molecule. Methods for using the tumor imaging agents and kits containing the tumor imaging agents or components suitable for production of the tumor imaging agents are also provided.

19 Claims, 3 Drawing Sheets

Analysis: Channel A

| Peak No. | Time | Type | Height (µV) | Area(µV-sec) | Area% |
|---|---|---|---|---|---|
| 1 | 0.873 | N1 | 1151 | 322364 | 0.554 |
| 2 | 1.830 | N2 | 435613 | 16133566 | 27.769 |
| 3 | 3.096 | N3 | 83999 | 1453500 | 2.501 |
| 4 | 3.191 | N4 | 81683 | 812867 | 1.399 |
| 5 | 3.558 | N5 | 75705 | 1604953 | 2.762 |
| 6 | 4.131 | N6 | 66433 | 2468158 | 4.248 |
| 7 | 13.125 | N7 | 14474 | 20136526 | 34.659 |
| 8 | 15.826 | N1 | 160489 | 4282915 | 7.371 |
| 9 | 17.330 | N2 | 42142 | 8650566 | 14.889 |
| 10 | 18.576 | X3 | 89134 | 2233271 | 3.843 |
| Total Area | | | | 58098686 | 99.995 |

TUMOR IMAGING AGENTS, METHODS AND KITS

CROSS-REFERENCE TO RELATED APPLICATION

This application is a continuation in part of PCT/US96/20675 filed Dec. 27, 1996.

The present invention is in the field of nuclear medicine. More specifically, the invention relates to diagnostic imaging of tumors.

BACKGROUND OF THE INVENTION

Clinical imaging technology plays a significant role in diagnosis of injuries and disease processes. Many parts of the human body can now be examined for diagnostic purposes using a variety of imaging techniques. Radiography has long been used to image body parts through which externally generated x-rays are transmitted. Computerized axial tomography (CAT) provides cross-sectional x-ray images of a plane of the body. Specific tissues or organs may be targeted in positron emission tomography (PET), single photon emission computed tomography (SPECT), and gamma scintigraphy. In PET, SPECT, and gamma scintigraphy, radiopharmaceutical agents capable of being sequestered (concentrated) to some degree in the target tissue or organ are internally administered to the patient, and images are generated by detecting the radioactive emissions from the concentrated radiopharmaceutical agent. Some of the radiopharmaceutical agents currently used for imaging include nuclides such as $^{201}$Tl, $^{99m}$Tc, $^{133}$Xe, and the like; chelates of nuclides; radiolabeled metabolic agents such as $^{11}$C-deoxy-D-glucose, $^{18}$F-2-fluorodeoxy-D-glucose, [1-$^{11}$C]- and [$^{123}$I]-β-methyl fatty acid analogs, $^{13}$N-ammonia, and the like; infarct avid agents such as $^{99m}$Tc-tetracycline, $^{99m}$Tc-pyrophosphate, $^{203}$Hg-mercurials, $^{67}$Ga-citrate, and the like; and radiolabeled ligands, proteins, peptides, and monoclonal antibodies. Whole cells such as erythrocytes, platelets, leukocytes, and other cells may also be labeled with a radionuclide and function as radiopharmaceutical agents.

The amount and type of clinical information that can be derived from PET, SPECT, and gamma scintigraphic images is related in part to the ability to concentrate the radiopharmaceutical agent in the target tissue or organ. Although many radiopharmaceuticals are available for clinical use, the resolution of the image generated may be limited depending on various factors. The resolution of a particular imaging agent for imaging diseased or injured tissue depends in part on the affinity of the radiopharmaceutical for the site of injury or disease as compared to its affinity for surrounding healthy tissue.

Radiopharmaceuticals are used to diagnose and treat tumors.

D. R. Elmaleh, et al. (1984) *Proc. Natl. Acad. Sci. USA* 81, 918–921 discloses $^{99m}$Tc-labeled Ap$_4$A ($^{99m}$Tc-Ap$_4$A) used to image tumors implanted into rats. The method used to chelate the $^{99m}$Tc to the Ap$_4$A in this study yielded a mixture, in which $^{99m}$Tc was attached to the Ap$_4$A-dinucleotide and which also may have contained unchelated $^{99m}$Tc. This study was based on the premise that some human tumor cells are permeable to exogenous ATP and ADP, and that these cells incorporate the intact nucleotides in intracellular pools, in contrast to normal cells. Ap$_4$A was shown to permeate into hepatoma cells but not into a number of untransformed mammalian cell lines. In addition to accumulating in implanted tumors, the $^{99m}$Tc-Ap$_4$A in the 1984 study also accumulated in kidney, liver, bone, muscle, and lung.

SUMMARY OF THE INVENTION

Radionuclide-labeled nucleotide polyphosphates accumulate with high specificity in tumors, and one embodiment of the invention generally features tumor imaging agents which include a radionuclide associated with a nucleotide polyphosphates, the latter being a targeting moiety. The imaging agent has an improved ratio of targeted to untargeted radioactivity, as a result of the use of a co-eluant such a mannitol.

In another embodiment, the invention provides a tumor imaging agent that includes a radionuclide associated with a nucleotide polyphosphate targeting moiety. The imaging agent typically is eluted with an eluant as described herein, and the formulation of the agent may include traces of that agent.

Typically, the targeting moiety is a residue of a targeting precursor; for example, a targeting precursor is reacted with a labeling entity which includes the radionuclide and a chelator for the radionuclide. The imaging agent is the reaction product which includes a residue of the targeting precursor and the chelator, in association with the radionuclide. The association may involve one or more of: chelation, co-valent bonding or electrostatic bonding, or it may involve other forces or combination of forces which maintains the nucleoside in spatial proximity to a targeting molecule. The imaging agent may be the reaction product of the above defined targeting precursor with a radionuclide-containing moiety, and such reaction may involve the formation of a chelate or a co-valent reaction product, or a product in which both chelation and co-valent bonds are involved. Typically, the targeting precursor is a molecule of the formula A) or formula B), or dimers or trimers thereof such as the molecules of formulas C), or D):

A) $Nu_1\text{-}(p)_n\text{-}X$

B) $Nu_1\text{-}(p)_n\text{-}X\text{-}(p)_m\text{-}Nu_2$

C) $Nu_1\text{—}(p)_n\text{—}X_1\text{—}(p)_m\text{—}Nu_2$
$\qquad\qquad\qquad |$
$Nu_3\text{—}(p)_r\text{—}X_2\text{—}(p)_q\text{—}Nu_4,$ D) $Nu_1\text{—}(p)_n\text{—}X_1\text{—}(p)_m\text{—}Nu_2$
$\qquad\qquad\qquad |$
$\qquad\qquad\qquad X_3$
$\qquad\qquad\qquad |$
$Nu_3\text{—}(p)_r\text{—}X_2\text{—}(p)_q\text{—}Nu_4,$ wherein,
(1) each of $Nu_1$–$Nu_4$ is an independently selected nucleoside;
(2) p is selected from the group consisting of a phosphate moiety, a phosphorothioate moiety, an alkylphosphonate moiety, a phosphorodithioate moiety, a phosphoramidate moiety, an aminoalkylphosphoramidate moiety, an aminoalkylphophotriester moiety, an aminoalkylphosphorothioamidate moiety, and a thiophosphate moiety;
(3) each of X, $X_1$, $X_2$, and $X_3$ is selected from the group consisting of an alkyl group, a halogenated alkyl group, a nitrogen-containing alkyl group, a sulfur-containing alkyl group, an alkylene group, a halogenated alkylene group, a nitrogen-containing alkylene group, and a sulfur-containing alkylene group;
(4) (n+m) is from 2 to 8; and (r+q) is from 2 to 8.

Other agents (or residues of them reacted with the targeting moiety) to promote chelation or bonding may be present in the imaging agent.

In a preferred formula according to B), X is not optional, and Nu, and $Nu_2$ are the same and are adenosine, guanine, cytidine, thymidine, uracil, or inosine. Preferably, at least one of $Nu_1-N_4$ (most preferably each of $Nu_{1-Nu4}$) is adenosine. The preferred moieties for X (when it is present) are alkyl moieties or chloroalkyl moieties, and p is preferably a phosphate moiety. When X is not present, the radionuclide-containing structure may be chelated via an oxygen atom of the phosphates(). Preferably, the nucleoside is adenosine, p is a phosphate, n=2, and m=2.

The radionuclide (Z) which is ultimately associated or complexed with the targeting precursor may be $^{123}I$, $^{99m}Tc$, $^{18}F$, $^{68}Ga$, $^{62}Cu$, and $^{111}In$, although $^{99m}Tc$ is preferred. If the radionuclide is associated via an optional chelating structure (R), particularly for $^{99m}Tc$, the chelating structure may be an $-N_2S_2$ structure, an $-NS_3$ structure, an $-N_4$ structure, an isonitrile, a hydrazine, an HYNIC (hydrazinonicotinic acid) containing structure, a 2-methylthiolnicotinic acid containing structure, a phosphorus containing group, or a carboxylate group. In one specific embodiment, Z is $^{99m}Tc$, and it is part of a $^{99m}Tc$ complex having the following formula:

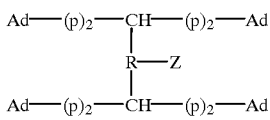

where Ad is adenosine, p is $PO_2H$, and R is a complexing moiety.

The above agents may be administered to image tumors tissue in a mammal. A specific imaging method detects tumors by administering the imaging agent to the mammal and detecting the spatial distribution of the agent. Differential accumulation of the agent is indicative of a tumor.

The invention also features kits for tumor imaging which comprises the imaging agent. The kit may include a chelating agent and/or an auxiliary molecule selected from the group consisting of mannitol, gluconate, glucoheptonate, and tartrate; and a tin-containing reducing agent, such as $SnCl_2$ or tin tartrate.

BRIEF DESCRIPTION OF THE DRAWINGS

The foregoing and other objects of this invention, the various features thereof, as well as the invention itself, may be more fully understood from the following description, when read together with the accompanying drawings in which.

DETAILED DESCRIPTION OF THE PREFERRED EMBODIMENTS

Figure 1:
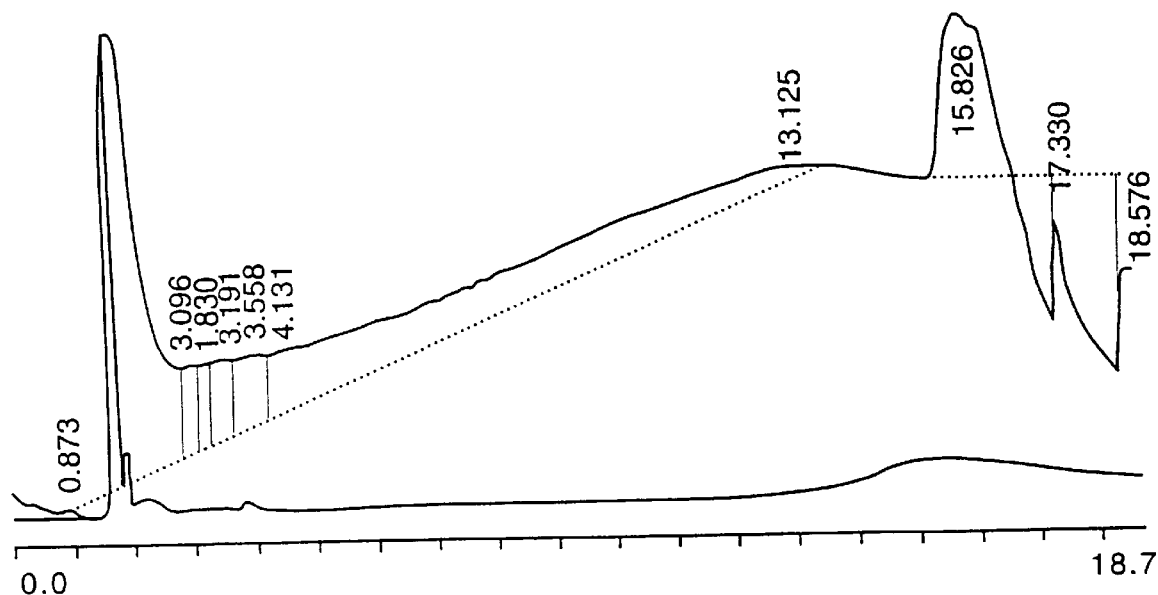
FIG. 1 shows an HPLC chromatogram of a reaction mixture obtained when 50 mg mannitol was used as an auxiliary molecule. Peaks of the elution profile are extrapolated, with areas under the peaks of the chromatogram tabulated below the elution profile.

The patent and scientific literature referred to herein establishes the knowledge that is available to those with skill in the art. The issued U.S. patents and allowed applications cited herein are hereby incorporated by reference.

The present invention provides novel tumor imaging agents in which analogs of nucleotide polyphosphates are associated with a radionuclide. The imaging agents of the invention specifically accumulate in tumors.

The imaging agents of the invention contain a targeting molecule which specifically accumulates in tumors. In general, preferred targeting molecules have the formula (or dimers or other multimers of it)

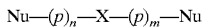

wherein Nu is a nucleoside selected from the group consisting of adenosine, guanine, cytidine, thymidine, uracil, and inosine; p is selected from the group consisting of a phosphate moiety, a phosphorothioate moiety, an alkylphosphonate moiety, a phosphorodithioate moiety, a phosphoramidate moiety, an aminoalkylphosphoramidate moiety, an aminoalkylphosphotriester moiety, and an aminoalkylphosphorothioamidate moiety; X is selected from the group consisting of an oxygen, an alkyl group, a halogenated alkyl group, a nitrogen-containing alkyl group, a sulfur-containing alkyl group, an alkylene group, a halogenated alkylene group, a nitrogen-containing alkylene group, and a sulfur-containing alkylene group, and (n+m) is from 2 to 8. The formulations of more than one nuclide-labeled targeting molecule.

Any nucleoside may be used as the "Nu" component of the targeting molecule. In addition to the ribonucleosides listed above, the "Nu" component of the targeting molecule may be a deoxynucleoside, a unsubstituted ribonucleoside, or a substituted deoxyribonucleoside, a substituted ribonucleoside, or a substituted deoxyribonucleoside. Substitutions may occur in accordance with the invention on the nucleic acid base portion of the nucleoside or on the sugar portion of the nucleoside. Sugars other than ribose or deoxyribose may also be present in the "Nu" component of the targeting molecule. Preferably, the nucleoside of the targeting molecule is adenosine.

Any molecule may be used as the "p" moiety to link the nucleoside components of the targeting molecule. The targeting molecule may contain synthetic internucleoside linking moieties other than the "p" moieties listed above, in which the "p" moiety is a substituted phosphate. For example, the substituted phosphate "p" moiety may contain one of more alkyl groups, carbamate groups, acetamidate groups, and the like. The "p" moiety may additionally be a non-phosphorus containing group such as a carboxymethyl ester or a carbonate, so long as the conformation of the resulting targeting molecule approximates that of a regulatory dinucleoside such as $Ap_4A$.

Any moiety may be used as the "X" component of the targeting molecule, so long as the conformation of the resulting targeting molecule approximates that of a regulatory dinucleoside such as $Ap_4A$ or dimers of $Ap_4A$.

Methods for synthesizing the targeting molecule are generally set forth in G. M. Blackburn, et al. (1986) in *Biophosphates and Their Analogues—Synthesis, Structure, Metal and Activity*, eds. Bruzik, K. S. & Stec, W. J. (Elsevier, amsterdam) pp. 451–464; G. M. Blackburn, et al. (1987) *Nucleic Acids Res.* 17, 6991–7004; A. Guranowski, et al. (1987) Biochemistry 26, 3425–3429; and G. M. Blackburn, et al. (1992) in *Dinucleoside Polyphosphates*, ed. McLennan, A. G. (CRC, Boca Raton, Fla.) Chapter 11.

In accordance with the invention, the targeting molecule is in association with (spatial proximity to) the nuclide. Spatial proximity between the targeting molecule and the nuclide may be effected in any manner which preserves the specificity of the targeting molecule for its target tissue. For example, spatial proximity between the nuclide and the targeting molecule may be effected by a covalent or non-covalent chemical bond. Such a chemical bond may be effected through a chelating substance and/or an auxiliary molecule such as mannitol, gluconate, glucoheptonate, tartrate, and the like. Alternatively, spatial proximity between the nuclide and the targeting molecule may be effected by incorporating the nuclide and the targeting molecule in a micelle or liposome, in such a way that the affinity of the targeting molecule for its target tissue is maintained. Spatial proximity between the nuclide and the targeting molecule may also be effected by attaching the nuclide and the targeting molecule to a matrix such as a microsphere or liposomes.

Those skilled in the art will recognize that there are a number of ways to synthesize the imaging agents. In one synthesis, Nu—$p_2$—CHCl—$p_2$Nu is reacted with X—R, where X is defined as $X_{1-3}$, above, and R is a radionuclide or a radionuclide chelating agent, such as a $^{99m}$Tc chelating agent. Typical $^{99m}$Tc chelating agents include allyl or aryl amines or alkyl or aryl thiols. Other $^{99m}$Tc chelating groups include $N_2S_2$, $S_4$. A precursor will be formed which contains the —R chelating agent, which in turn is reacted with $^{99m}$Tc from a standard $^{99m}$Tc reduction kit. For example, when —R is an alkyl thiol, the —$NS_3$ chelating reaction forms:

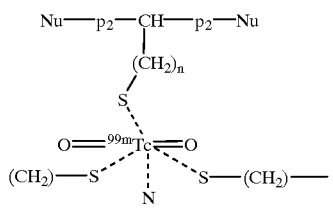

If the composition includes a chelating structure, particularly for $^{99m}$Tc, the chelating structure may be an $N_2S_2$ structure, an —$NS_3$ structure, an N. structure, an isonitrile, a hydrazine, a HYNIC (hydrazinonicotinic acid) group, a phosphorus containing group, or a carboxylate group. Those skilled in the art will understand that a great many other chelating reactions may be used.

The imaging agents described above may contain any radionuclide in accordance with the invention. Preferably, the imaging agents of the invention contain radionuclides suitable for use in PET or SPECT imaging. More preferably, the radionuclide (Z) used in the imaging agent is a radionuclide selected from the group consisting of $^{123}$I, $^{99m}$Tc, $^{18}$F, $^{68}$Ga, $^{62}$Cu, $^{111}$In, and the like. Such radionuclides may be incorporated into the imaging agent by covalent bonding directly to an atom of the targeting molecule, or the radionuclide may be non-covalently or covalently associated with the targeting molecule through a chelating structure or through an auxiliary molecule such as mannitol, gluconate, glucoheptonate, tartrate, and the like. When a chelating structure is used to provide spatial proximity between the radionuclide and the targeting molecule, the chelating structure may be directly associated with the targeting molecule or it may be associated with the targeting molecule through an auxiliary molecule such as mannitol, gluconate, glucoheptonate, tartrate, and the like.

Any suitable chelating structure may be used to provide spatial proximity between the radionuclide and the targeting molecule of the agent through covalent or non-covalent association. Many such chelating structures are known in the art. Preferably, the chelating structure is an $N_2S_2$ structure, an $NS_3$ structure, an $N_4$ structure, an isonitrile-containing structure, a hydrazine containing structure, a HYNIC (hydrazinonicotinic acid) group-containing structure, a 2-methylthiolnicotinic acid group-containing structure, a carboxylate group containing structure, and the like. In some cases, chelation can be achieved without including a separate chelating structure, because the radionuclide chelates directly to atom(s) in the targeting moiety, for example to oxygen atoms in the phosphate group(s) or in carboxylate group(s).

The chelating structure, auxiliary molecule, or radionuclide may be placed in spatial proximity to any position of the targeting molecule which does not interfere with the interaction of the targeting molecule with its receptor in tumors. The chelating structure, auxiliary molecule, or radionuclide may be covalently or non-covalently associated with any moiety of the targeting molecule except the receptor-binding moiety. For example, the chelating structure, auxiliary molecule, or radionuclide may be associated with the phosphate moiety of the targeting molecule, with the —X— moiety of the targeting molecule.

Radionuclides may be placed in spatial proximity to the targeting molecule using known procedures which effect or optimize chelation, association, or attachment of the specific radionuclide to ligands. For example, when $^{123}$I is the radionuclide, the imaging agent may be labeled in accordance with the known radioiodination procedures such as direct radioiodination with chloramine T, radioiodination exchange for a halogen or an organometallic group, and the like. When the radionuclide is $^{99m}$Tc, the imaging agent may be labeled using any method suitable for attaching $^{99m}$Tc to a ligand molecule. Preferably, when the radionuclide is $^{99m}$Tc, an auxiliary molecule such as mannitol, gluconate, glucoheptonate, or tartrate is included in the labeling reaction mixture, with or without a chelating structure. More preferably, $^{99m}$Tc is placed in spatial proximity to the targeting molecule by reducing $^{99m}$TcO$_4$ with tin in the presence of mannitol and the targeting molecule. When Ap$_4$A or an analog of Ap$_4$A is the targeting molecule, the preferably made by reducing about fifty to 100 mCi $^{99m}$TcO$_4$ with 0.05–1 mg SnCl$_2$ in the presence of about 1 to 20 mg of mannitol, for each mg of Ap$_4$A or Ap$_4$A analog. More preferably, for each mg of Ap$_4$A or Ap$_4$A analog, about 0.05 mg SnCl$_2$ and about 10 mg mannitol are used to reduce the $^{99m}$TcO$_4$.

Other reducing agents, e.g., tin tartrate, may also be used to make the imaging agent of the invention. An exemplary procedure for placing $^{99m}$Tc in spatial proximity to Ap$_4$A and the Ap$_4$A analog in which the "X" moiety is —CHCl— is set forth in Example 1.

After the labeling reaction is complete, the reaction mixture may optionally be purified using one or more high performance liquid chromatography (HPLC) steps. Any suitable HPLC system may be used if a purification step is performed, and the yield of imaging agent obtained from the HPLC step may be optimized by varying the parameters of the HPLC system, as is known in the art. Any HPLC parameter may be varied to optimize the yield of the imaging agent of the invention. For example, the pH may be varied, e.g., raised, to decrease the elution time of the peak corresponding to the imaging agent of the invention.

The invention as embodied in a kit for imaging comprises one or more of the imaging agents described above, in combination with a pharmaceutically acceptable carrier such as human serum albumin. Human serum albumin for use in the kit of the invention may be made in any way, for example, through purification of the protein from human serum or though recombinant expression of a vector containing a gene encoding human serum albumin. Other substances may also be used as carriers in accordance with this embodiment of the invention, for example, detergents, dilute alcohols, carbohydrates, auxiliary molecules, and the like. The kit of the invention may of course also contain such other items as may facilitate its use, such as syringes, instructions, reaction vials, and the like.

In one embodiment, a kit according to the invention contains from about 1 to about 30 mCi of the radionuclide-labeled tumor imaging agent described above, in combination with a pharmaceutically acceptable carrier. The kits of the invention may include radionuclide-labeled $Ap_4A$ analogs. The tumor imaging agent and carrier may be provided in solution or in lyophilized form. When the tumor imaging agent and carrier of the kit are in lyophilized form, the kit may optionally contain a sterile and physiologically acceptable reconstitution medium such as water, saline, buffered saline, and the like.

In another embodiment, the kit of the invention may contain the unlabeled targeting molecule which has been covalently or non-covalently combined with a chelating agent; an auxiliary molecule such as mannitol, gluconate, glucoheptonate, tartrate, and the like; and a reducing agent such as $SnCl_2$ or tin tartrate. In this embodiment, the kit may include unlabeled $Ap_4A$ or an unlabeled $Ap_4A$ analog. The unlabeled targeting molecule/chelating agent and the auxiliary molecule may be present as separate components of the kit or they may be combined into one kit component. The unlabeled targeting molecule/chelating agent, the auxiliary molecule, and the reducing agent may be provided in solution or in lyophilized form, and these components of the kit of the invention may optionally contain stabilizers such as NaCl, silicate, phosphate buffers, ascorbic acid, gentisic acid, and the like. Additional stabilization of kit components may be provided in this embodiment, for example, by providing the reducing agent in an oxidation-resistant form. Determination and optimization of such stabilizers and stabilization methods are well within the level of skill in the art. When the unlabeled targeting molecule/chelating agent of this embodiment are in lyophilized form, the kit may optionally contain a sterile and physiologically acceptable reconstitution medium such as water, saline, buffered saline, and the like. The amounts of unlabeled targeting molecule/chelating agent, auxiliary molecule, and reducing agent in this embodiment are optimized in accordance with the methods for making the tumor imaging agent set forth above. Radionuclides, such as $^{99m}Tc$ from a commercially available $^{99m}Mo/^{99m}Tc$ generator or commercially available $^{123}I$, may be combined with the unlabeled targeting molecule/chelating agent and the reducing agent for a time and at a temperature sufficient to chelate the radionuclide to the targeting molecule/chelating agent, and the imaging agent thus formed is injected into the patient.

The tumor imaging agents of the invention may be used in accordance with the methods of the invention by those of skill in the art, e.g., by specialists in nuclear medicine, to image tissue in a mammal. Any mammalian tumor may be imaged the imaging agents of the invention. For example, the imaging agents of the invention are suitable for imaging breast tumors, prostate tumors melanomas, colon tumors, etc. The methods of the invention may employ radionuclide-labeled $Ap_4A$ or a radionuclide-labeled $Ap_4A$ analog.

Images are generated by virtue of differences in the spatial distribution of the imaging agents which accumulate in the various tissues and organs of the mammal. The spatial distribution of the imaging agent accumulated in a mammal, in an organ, or in a tissue may be measured using any suitable means, for example, a gamma camera, a PET apparatus, a SPECT apparatus, and the like. Some tumors may be evident when a less intense spot appears within the image, for example, within a $^{99m}Tc$-$Ap_4A$-labeled indicating the presence of tissue in which a lower concentration of imaging agent accumulates relative to the concentration of imaging agent which accumulates in the tumor. Alternatively, a tumor might be detectable as a more intense spot within the image, indicating a region of enhanced concentration of the imaging agent at the site of the tumor relative to the concentration of agent which accumulates in surrounding tissue. The extent of accumulation of the imaging agent may be quantified using known methods for quantitating radioactive emissions. A particularly useful imaging approach employs more than one imaging agent to perform simultaneous studies.

The imaging agents of the invention are used in the following manner. An effective amount of an imaging agent comprising at least one targeting molecule and a nuclide (from 1 to 50 mCi) may be combined with a pharmaceutically acceptable carrier for use in imaging studies. In accordance with the invention, "an effective amount" of the imaging agent of the invention is defined as an amount sufficient to yield an acceptable image using equipment which is available for clinical use. An effective amount of the imaging agent of the invention may be administered in more than one injection. Effective amounts of the imaging agent of the invention will vary according to factors such as the degree of susceptibility of the individual, the age, sex, and weight of the individual, idiosyncratic responses of the individual, the dosimetry. Effective amounts of the imaging agent of the invention will also vary according to instrument and film-related factors. Optimization of such factors is well within the level of skill in the art.

As used herein, "pharmaceutically acceptable carrier" includes any and all solvents, dispersion media, coatings, antibacterial and antifungal agents, isotonic agents, absorption delaying agents, and the like. The formulation used in the present invention may also contain stabilizers, preservatives, buffers, antioxidants, or other additives known to those of skill in the art. The use of such media and agents for pharmaceutically active substances is well known in the art. Supplementary active compounds can also be incorporated into the imaging agent of the invention. The imaging agent of the invention may further be administered to an individual in an appropriate diluent or adjuvant, co-administered with enzyme inhibitors or in an appropriate carrier such as human serum albumin or liposomes. Pharmaceutically acceptable diluents include sterile saline and other aqueous buffer solutions. Adjuvants contemplated herein include resorcinols, non-ionic surfactants such as polyoxyethylene oleyl ether and n-hexadecyl polyethylene ether. Enzyme inhibitors include pancreatic trypsin inhibitor, diethylpyrocarbonate, and trasylol. Liposomes inhibitors include water-in-oil-in-water CGF emulsions as well as conventional liposomes (Strejan et al. (1984) *J. Neuroimmunol.* 7, 27).

Preferably, the imaging agent of the invention is administered intravenously, and the imaging agent will be formulated as a sterile, pyrogen-free, parenterally acceptable aqueous solution. The preparation of such parenterally acceptable solutions, having due regard to pH, isotonicity, stability, and the like, is within the skill in the art. A preferred formulation for intravenous injection should contain, in addition to the imaging agent, an isotonic vehicle such as Sodium Chloride Injection, Ringer's Injection, Dextrose Injection, Dextrose and Sodium Chloride Injection, Lactated Ringer's Injection, or other vehicle as known in the art.

The amount of imaging agent used for diagnostic purposes and the duration of the imaging study will depend upon the nature and severity of the condition being treated, on the nature of therapeutic treatments which the patient has undergone, and on the idiosyncratic responses of the patient. Ultimately, the attending physician will decide the amount of imaging agent to administer to each individual patient and the duration of the imaging study.

The following examples are included for illustrative purposes only and are not intended to limit the scope of the invention.

EXAMPLE 1

SYNTHESIS OF $^{99m}$Tc-Ap$_4$A-coligand (mannitol or gluconate) and $^{99mTc-Ap}{}_2$CHClp$_2$A-coligand (mannitol or gluconate)

Fifty to 100 mCi $^{99m}$TcO$_4$ was obtained from a $^{99}$Mo/$^{99m}$Tc generator (DuPont Merck, Billerica, Mass.) in 1.5 ml sterile water and mixed with a solution of one mg Ap$_4$A (Sigma, St. Louis, Mo.), 50 mg mannitol, and 100 μg SnCl$_2$ in 200 μl sterile water. The solution was stirred and allowed to react for ten minutes at room temperature. The reaction mixture was then HPLC purified by adsorption onto a 5 mm diameter, 25 cm long C8-ODS reverse phase column (Waters, Milford, Mass.) and elution with CH$_3$CN: buffer (20:80). The buffer for the elution step contained 3.1 ml concentrated H$_3$PO$_4$, 3.9ml t-butylammonium hydroxide, which were combined and titrated with NaOH to pH 2.4. FIG. 1 shows an elution profile using this procedure, with unlabeled material shown by the bold line (measured by A$_{254}$), and labeled material shown in the fainter solid line (measured by τ-emissions). The dotted line in FIG. 1 is the radioactivity elution profile. The radioactive peak eluting at 15.826 minutes is $^{99m}$Tc-Ap$_4$A, which was injected into skid mice as set forth in Example 2, to image tissue. The radioactive peak eluting at 1–3 minutes on this chromatogram was $^{99m}$Tc-mannitol, which was used as a control in the experiments described in Example 2.

A similar procedure was used to label the Ap$_4$A analog of the formula:

A—(p)$_2$—CHCl—(p)$_2$—A with $^{99m}$Tc.

Figure 2:
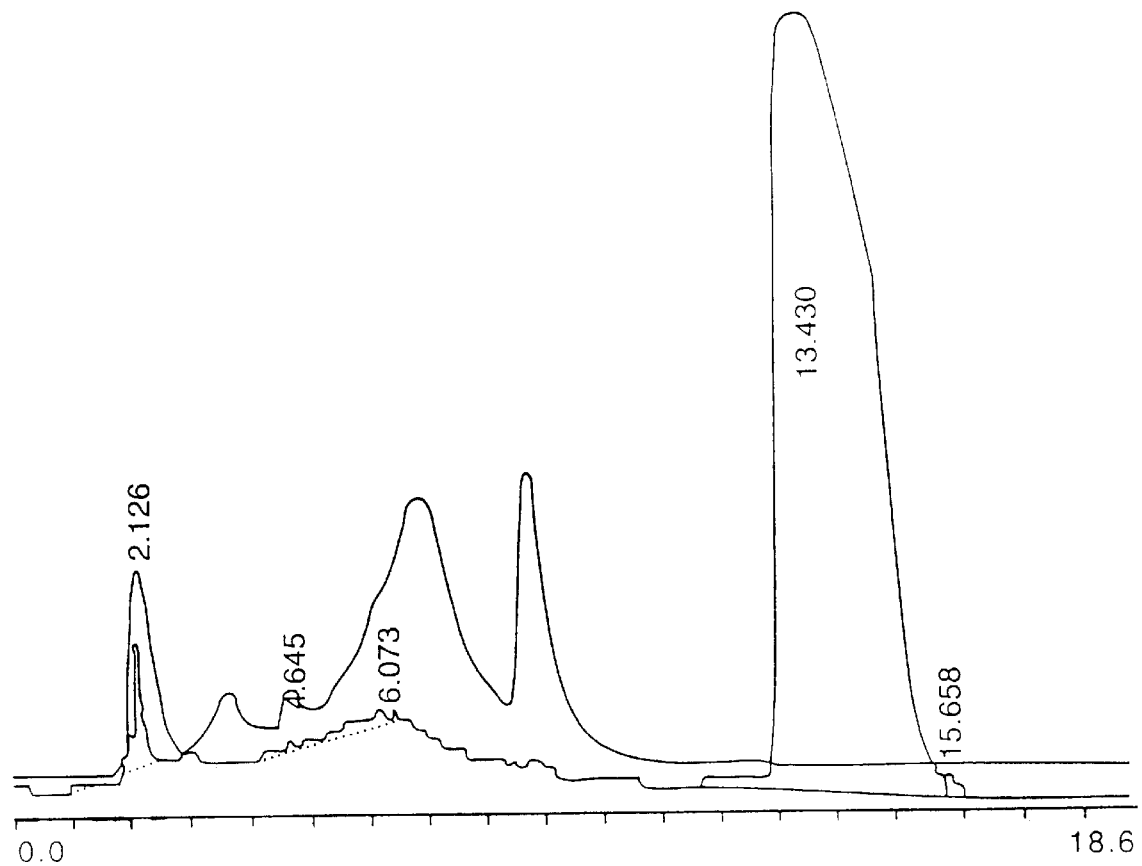
FIG. 2 shows an HPLC chromatogram of an alternative reaction mixture, in which 10 mg mannitol was used as an auxiliary molecule. Peaks of the elution profile are extrapolated, with areas under the peaks of the chromatogram tabulated below the elution profile.

FIG. 2 is a reverse phase HPLC elution profile of a $^{99m}$Tc-Ap$_4$A preparation in which 10 mg mannitol and 40 μg SnCl$_2$ was used to perform the reduction of one mg Ap$_4$A. This reaction mixture was also stirred and allowed to react for ten minutes at room temperature. HPLC purification of the reaction mixture was performed as above, with the exception that the CH$_3$CN:buffer ratio was 15:85 and the elution buffer contained 3.0 ml concentrated H$_3$PO$_4$ and 3.36 ml t-butylammonium hydroxide titrated with NaOH to pH 3.4. FIG. 2 shows the elution profile of the reaction mixture, the peak eluting at 13.430 minutes corresponding to $^{99m}$Tc-Ap$_4$A.

When one mg mannitol was used as an auxiliary molecule in the labeling reaction, very low yields $^{99m}$Tc-Ap$_4$A were obtained.

EXAMPLE 2

AP4A was labeled with Tc-99m by reaction with Tc-99m gluconate and the product was purified by reverse phase HPLC C-8-0ds column (0.5×25 cm). The product was eluted with CH$^3$CN/buffer (20:80 by volume). The buffer was prepared by mixing H$^3$PO$^4$ (3.1 ml) with t-butylammonium hydroxide (3.9 ml) and adjusting the pH to 2.4 by adding additional t-butylammonium hydroxide. In the HPLC system that was used Tc-99m-AP4A-glyco eluted with a retention time of 16 minutes. Radiochemical yields was 10–30% and radiochemical purity was >95%.

EXAMPLE 3

IMAGING TUMORS

Figure 3:
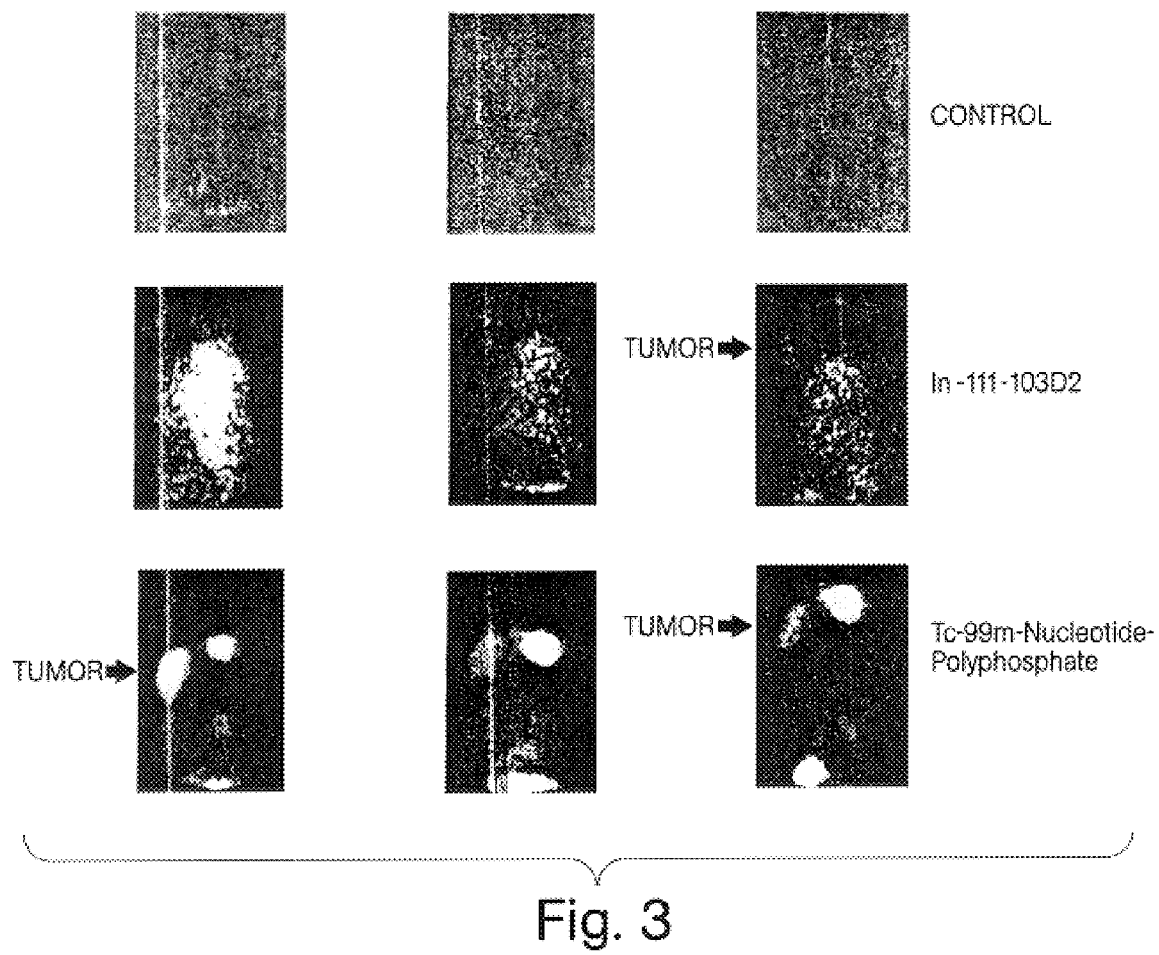
FIG. 3 is a set of radio-images of tumors in skid mice.

A tumor model was prepared by inoculating BT20 human breast tumor cells in the shoulder region of skid mice. When the tumors reached≈0.5cm, groups of mice (n=14) were injected with 0.5 mCi of Tc-99m-AP4A-gluco or Tc-99,\m-mannitol (control), prepared as described above. At 0,5, 3 and 5 hours, gamma camera images were acquired and tumor-to-contralateral ratios were calculated. At 5 and 8 hours, groups of 9 and 5 animals were sacrificed and biodistribution was measured. In all animals, the tumors were clearly visualized at 0.5 hours, and T/B (tumor to blood ratio) increased in the later images. At all three imaging times, there was a very low level of tracer accumulating in normal tissues. The biodistribution studies demonstrated high concentrations (% ID/gram) of TC-99m-AP4-A-manitol in the tumors: 7.3+3.2 and 11.0+2.8 at five and eight hours, respsectively. In contrast, the concentration of Tc-99m-mannitol was 0.9%. FIG. 3 is an image produced generally using the above technique.

What is claimed is:

1. A tumor imaging agent comprising a radionuclide associated with a targeting moiety by way of an auxiliary molecule, said targeting moiety comprising a residue of nucleotide polyphosphate precursor having formula A), B), C), or D):

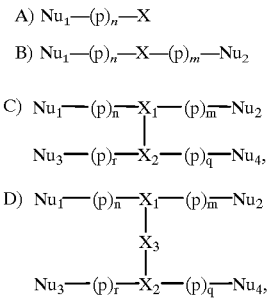

A) Nu$_1$—(p)$_n$—X

B) Nu$_1$—(p)$_n$—X—(p)$_m$—Nu$_2$

C) Nu$_1$—(p)$_{\overline{n}}$—X$_1$—(p)$_{\overline{m}}$—Nu$_2$
   |
   Nu$_3$—(p)$_{\overline{r}}$—X$_2$—(p)$_{\overline{q}}$—Nu$_4$, D) Nu$_1$—(p)$_{\overline{n}}$—X$_1$—(p)$_{\overline{m}}$—Nu$_2$
   |
   X$_3$
   |
   Nu$_3$—(p)$_{\overline{r}}$—X$_2$—(p)$_{\overline{q}}$—Nu$_4$, wherein, in the above formulas A)–D),
(1) each of Nu$_1$–Nu$_4$ is adenosine;
(2) p is a phosphate moiety;
(3) X is an alkyl moiety or a choroalkyl moiety and X$_1$, X$_2$, and X$_3$ are absent; and
(4) (n+m) is from 2 to 8; and (r+q) is from 2 to 8.

2. The agent of claim 1 further comprising a radionuclide selected from the group consisting of $^{123}$I, $^{99m}$Tc, $^{18}$F, $^{68}$Ga, $^{62}$Cu, and $^{111}$In.

3. The agent of claim 1, wherein said imaging agent comprises the product of combining said polyphosphate precursor with a chelating structure which chelates said radionuclide.

4. The agent of claim 3, wherein the chelating structure is selected from the group consisting of an —N$_2$S$_2$ structure, an —NS$_3$ structure, an —N$_4$ structure, an isonitrile, a hydrazine, a HYNIC group-containing structure, 2-methylthiolnicotinic acid-group, and a carboxylate group-containing structure.

5. The agent of any of claims 3–4, wherein the radionuclide is $^{99m}$Tc.

6. A tumor imaging agent comprising a radionuclide associated with a targeting moiety by way of an auxiliary molecule, said targeting moiety comprising a residue of nucleotide polyphosphate precursor having formula A), B), C), or D):

A) $Nu_1-(p)_n-X$

B) $Nu_1-(p)_n-X-(p)_m-Nu_2$

C) $Nu_1-(p)_{\overline{n}}-X_1-(p)_{\overline{m}}-Nu_2$
   $Nu_3-(p)_{\overline{r}}-X_2-(p)_{\overline{q}}-Nu_4,$ D) $Nu_1-(p)_{\overline{n}}-X_1-(p)_{\overline{m}}-Nu_2$
   $\quad\quad\quad\quad\quad|$
   $\quad\quad\quad\quad\quad X_3$
   $\quad\quad\quad\quad\quad|$
   $Nu_3-(p)_{\overline{r}}-X_2-(p)_{\overline{q}}-Nu_4,$ wherein, in the above formulas A)–D),
(1) each of $Nu_1$–$Nu_4$ is an independently selected nucleoside;
(2) p is a phosphate moiety;
(3) X is an alkyl moiety or a choroalkyl moiety and $X_1$, $X_2$, and $X_3$ are absent; and
(4) (n+m) is from 2 to 8; and (r+q) is from 2 to 8.

7. A tumor imaging agent comprising a complex of $^{99m}Tc$ having the formula:

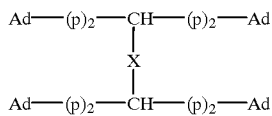

where Ad is adenosine, and p is $PO_2H$, and X is a $^{99m}Tc$-containing chelating moiety.

8. A method of imaging tumors in a mammal which comprises the steps of administering to the mammal the imaging agent of claim 1, or claim 7, and imaging the mammal to obtain an image.

9. The method of claim 8 in which the method detects a tumor in a mammal, said method comprising the steps of administering to the mammal the imaging agent and detecting the spatial distribution of the agent accumulated in the mammal's.

10. A method of imaging tumors in a mammal which comprises the steps of administering to the mammal the imaging agent of claim 6 and imaging the mammal to obtain an image.

11. The method of claim 8 further comprising reacting the polyphosphate precursor with a radionuclide containing moiety.

12. A kit for tumor imaging which comprises a supply of a targeting precursor, said targeting precursor having formula A), B), C), or D):

A) $Nu_1-(p)_n-X$

B) $Nu_1-(p)_n-X-(p)_m-Nu_2$

C) $Nu_1-(p)_{\overline{n}}-X_1-(p)_{\overline{m}}-Nu_2$
   $Nu_3-(p)_{\overline{r}}-X_2-(p)_{\overline{q}}-Nu_4,$ D) $Nu_1-(p)_{\overline{n}}-X_1-(p)_{\overline{m}}-Nu_2$
   $\quad\quad\quad\quad\quad|$
   $\quad\quad\quad\quad\quad X_3$
   $\quad\quad\quad\quad\quad|$
   $Nu_3-(p)_{\overline{r}}-X_2-(p)_{\overline{q}}-Nu_4,$ wherein, in the above formulas A)–D),
(1) each of $Nu_1$–$Nu_4$ is adennine;
(2) p is phosphate moiety;
(3) X is an alkyl moiety or a choroalkyl moiety and $X_1$, $X_2$, and $X_3$ are absent; and
(4) (n+m) is from 2 to 8; and (r+q) is from 2 to 8.

13. The kit of claim 12 further comprising a chelating agent, the chelating agent comprising:
   a) an auxiliary molecule selected from the group consisting of mannitol, gluconate, glucoheptonate, and tartrate; and
   b) a tin-containing reducing agent.

14. The kit of claim 12 further comprising a radionuclide selected from the group consisting of $^{123}I$, $^{99m}Tc$, $^{18}F$, $^{68}Ga$, $^{62}Cu$, and $^{111}In$.

15. The kit of claim 12, wherein said kit further comprises at least one chelating structure.

16. The kit of claim 15, wherein the chelating structure is selected from the group consisting of an —$N_2S_2$ structure, an —$NS_3$ structure, an —$N_4$ structure, an isonitrile, a hydrazine, a HYNIC group-containing structure, 2-methylthiolnicotinic acid-group, and a carboxylate group-containing structure.

17. The kit of any of claims 15 or 16 wherein the radionuclide is $^{99m}Tc$.

18. A kit for tumor imaging which comprises a supply of a targeting precursor, said targeting precursor having formula A), B), C), or D):

A) $Nu_1-(p)_n-X$

B) $Nu_1-(p)_n-X_1-(p)_m-Nu_2$

C) $Nu_1-(p)_{\overline{n}}-X_1-(p)_{\overline{m}}-Nu_2$
   $Nu_3-(p)_{\overline{r}}-X_2-(p)_{\overline{q}}-Nu_4,$ D) $Nu_1-(p)_{\overline{n}}-X_1-(p)_{\overline{m}}-Nu_2$
   $\quad\quad\quad\quad\quad|$
   $\quad\quad\quad\quad\quad X_3$
   $\quad\quad\quad\quad\quad|$
   $Nu_3-(p)_{\overline{r}}-X_2-(p)_{\overline{q}}-Nu_4,$ wherein, in the above formulas A)–D),
(1) each of $Nu_1$–$Nu_4$ is adennine;
(2) p is phosphate moiety;
(3) X is an alkyl moiety or a choroalkyl moiety and $X_1$, $X_2$, and $X_3$ are absent; and
(4) (n+m) is from 2 to 8; and (r+q) is from 2 to 8.

19. The agent of claim 6 which each of $Nu_1$—$Nu_4$ is independently selected from the group nucleosides consisting of adenosine, guanosine, cytidine, thymidine, uridine, and inosine.

* * * * *